United States Patent
Kimura

(10) Patent No.: US 8,102,533 B2
(45) Date of Patent: Jan. 24, 2012

(54) TOTAL REFLECTION ILLUMINATED SENSOR CHIP

(75) Inventor: Toshihito Kimura, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 249 days.

(21) Appl. No.: 12/625,014

(22) Filed: Nov. 24, 2009

(65) Prior Publication Data

US 2010/0128274 A1  May 27, 2010

(30) Foreign Application Priority Data

Nov. 25, 2008 (JP) ................................ 2008-299101

(51) Int. Cl.
*G01N 21/00* (2006.01)
(52) U.S. Cl. ..................................................... 356/445
(58) Field of Classification Search ........... 356/445–448
See application file for complete search history.

(56) References Cited

U.S. PATENT DOCUMENTS

| 2005/0179901 A1 | 8/2005 | Ostlin et al. |
| 2006/0109472 A1* | 5/2006 | Muraishi ....................... 356/445 |
| 2006/0159591 A1 | 7/2006 | Ohtsuka |

FOREIGN PATENT DOCUMENTS

| EP | 0411907 A2 | 2/1991 |
| JP | 10-78390 A | 3/1998 |
| WO | WO2008/139356 A1 | 11/2008 |

* cited by examiner

*Primary Examiner* — Michael P Stafira
(74) *Attorney, Agent, or Firm* — Birch, Stewart, Kolasch & Birch, LLP

(57) ABSTRACT

A total reflection illuminated sensor chip is employed to detect a target substance, by: supplying a sample containing the target substance onto a detecting portion formed on a surface of a dielectric prism, irradiating a measuring light beam onto the interface between the prism and the detecting portion through a transmitting surface of the prism such that conditions for total reflection are satisfied, and utilizing evanescent waves generated at the detecting portion. The sensor chip includes a protective member for protecting the transmitting surface. The protective member is provided a predetermined distance away from the transmitting surface to form a transmitting space, which is open at least toward the downward direction. The sensor chip is configured such that the interface can be irradiated by the measuring light beam that enters the transmitting space from below the transmitting space and passes through the transmitting surface.

18 Claims, 10 Drawing Sheets

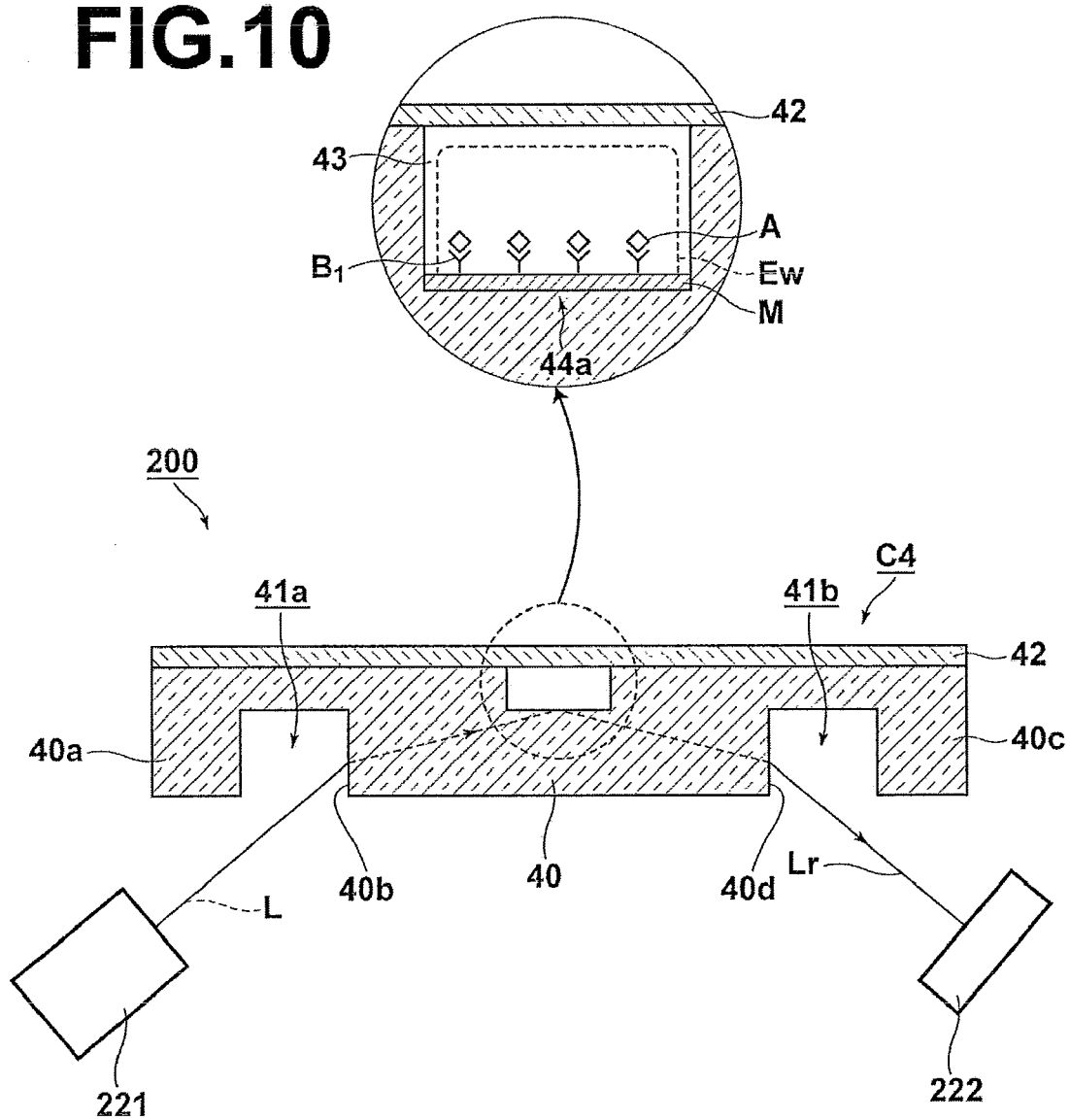

TOTAL REFLECTION ILLUMINATED SENSOR CHIP

BACKGROUND OF THE INVENTION

1. Field of the Invention

The present invention is related to a total reflection illuminated sensor chip, which is employed in a method for detecting substances within samples by utilizing evanescent waves.

2. Description of the Related Art

Conventionally, detecting methods that utilize evanescent waves or surface plasmon induced by totally reflected illumination are being focused on, in biological measurements for detecting proteins, DNA, and the like. Surface plasmon are compression waves of free electrons which are generated by the free electrons vibrating as a group at the surfaces of metals. Such detecting methods include SPFS (Surface Plasmon Field enhanced fluorescence Spectroscopy) measurement and SPR (Surface Plasmon Resonance) measurement, which employs attenuated total reflection due to surface plasmon resonance.

SPFS measurement is a method in which detection target substances are detected, by: generating evanescent waves on a metal film that functions as a detecting portion provided on a dielectric prism; exciting the detection target substances included in samples or fluorescent labels attached to the detection target substances by the evanescent waves; and detecting the fluorescence emitted by the detection target substance or the fluorescent labels (refer to Japanese Patent No. 3562912). The evanescent waves are generated on the metal film, by causing a measuring light beam to be totally reflected at the interface between the dielectric prism and the metal film provided thereon. SPFS measurement is easy to execute, and is capable of measuring a plurality of samples simultaneously. Further, the electric field enhancing effect of surface plasmon, which is generated by the evanescent waves resonating with free electrons in the metal film amplify the evanescent waves, which enables great fluorescent signals to be detected. Accordingly, SPFS measurement is widely used.

Meanwhile, SPR measurement is a method in which detection target substances are detected, by: varying the incident angle of light that enters the interface between a dielectric prism and a metal film that functions as a detecting portion provided on the dielectric prism; and detecting attenuation of light reflected at the interface to detect a change in the refractive index on the metal film (refer to U.S. Patent Application Publication No. 20060159591). For example, if antigens bind with antibodies which are immobilized on the metal film by antigen antibody reactions, the refractive index on the metal film becomes greater than that of the surrounding buffer. Accordingly, SPR measurement is detects the change in refractive index as a change in the SPR resonance angle (an incident angle at which the reflected light is attenuated). SPR measurement, which is a method for detecting refractive indices, is widely used as a method that enables reactions, binding amounts and analysis of binding speeds among biological molecules in real time without labeling.

In the aforementioned SPFS measurement and SPR measurement, measuring light beams are totally reflected at interfaces between dielectric prisms and a detecting portion. Therefore, dielectric prisms, on predetermined regions of which a detecting portion are formed, are commonly employed as sensor chips. Presently, dielectric prisms formed of plastic, which are less expensive and more easily molded than glass, are commonly employed. However, during conventional measurement operations, dielectric prisms are exposed during handling of sensor chips. Therefore, there is a problem that damage and contamination occurs at the surfaces through which measuring light beams enter the dielectric prisms, or at the surfaces through which light exits the dielectric prisms. Particularly, plastic dielectric prisms are softer than those formed of glass, and therefore the surfaces thereof are more likely to become damaged. In these cases, the damage and contamination generates noise due to absorption, attenuation, and scattering of measuring light beams, and the measurement accuracy deteriorates. Therefore, U.S. Patent Application Publication No. 20060159591 teaches a sensor unit equipped with a protective member that protects the surface of a dielectric prism through which measurement light beams enter or the surface through which light exits the dielectric prism.

There is demand for diagnostic sensor chips to be produced at low cost, and to be made thinner. However, the sensor unit disclosed in U.S. Patent Application Publication No. 20060159591 has a great number of parts, and therefore does not sufficiently meet this demand. Further, it is difficult to form a sensor unit, which includes a protective member having a small slit for transmitting light therethrough, thin.

SUMMARY OF THE INVENTION

The present invention has been developed in view of the foregoing circumstances. It is an object of the present invention to provide a total reflection illuminated sensor chip having a structure that protects the surface of a dielectric prism through which a measuring light beam enters or the surface of a dielectric prism through which light is output from damage and contamination, which is capable of realizing low cost production and capable of being formed thin.

A first total reflection illuminated sensor chip of the present invention is employed in a detecting method for detecting a detection target substance comprising the steps of: supplying a sample that includes the detection target substance onto a detecting portion formed on a surface of a dielectric prism, irradiating a measuring light beam onto the interface between the dielectric prism and the detecting portion through a first light transmitting surface of the dielectric prism such that conditions for total reflection are satisfied at the interface, and utilizing evanescent waves which are generated at the detecting portion due to the irradiation of the measuring light beam to detect the detection target substance, and is characterized by comprising:

the dielectric prism;

the detecting portion formed on the surface of the dielectric prism; and a first protective member for protecting the first light transmitting surface;

the first protective member being provided at a position which is a predetermined distance away from the first light transmitting surface so as to form a first light transmitting space, which is open at least toward the downward direction, between the first light transmitting surface and the first protective member; and the total reflection illuminated sensor chip being configured such that the interface can be irradiated by the measuring light beam that enters the first light transmitting space from below the first light transmitting space and passes through the first light transmitting surface.

In the present specification, the term "detecting portion" refers to a location at which the detection target substance is detected. For example, in the case that (a) a binding substance (antibodies, for example) that specifically binds with a detection target substance (antigens, for example) is immobilized on the dielectric prism, the region of the dielectric prism at which the binding substance is immobilized is the detecting portion. Alternatively, in the case that (b) a metal film for causing surface plasmon to be generated is formed on the dielectric prism, the metal film is the detecting portion.

The term "interface" between the dielectric prism and the detecting portion refers to a boundary surface between the refractive index of the dielectric prism and the refractive index of the detecting portion. Accordingly, in the case of (a) above, the "conditions for total reflection" refer to conditions for total reflection which are determined by the refractive indices of each of the dielectric prism and the substance on the dielectric prism (the binding substance, solutions, air, and the like). In the case of (b) above, the "conditions for total reflection" refer to conditions for total reflection which are determined by the refractive indices of each of the dielectric prism and the metal film.

The term "first light transmitting surface" refers to the surface of the dielectric prism that the measuring light beam passes through when entering the dielectric prism.

The phrase "detecting a detection target substance" refers not only to detecting the qualitative amounts, that is, whether the detection target substance is present, but also to detecting quantitative amounts of the detection target substance, and detecting the degree of activity thereof.

The phrase "protecting the first light transmitting surface" refers to protecting the first light transmitting surface from external factors that cause damage and contamination, such as fingers of operators contacting the first light transmitting surface.

The term "downward direction" refers to a negative direction along a z axis, which is perpendicular to an x-y plane that includes the interface between the dielectric prism and the metal film. The z axis is designated in a coordinate system as follows. A direction which is opposite a direction in which projected components of the measuring light beam travel toward a line of intersection between an incident surface that the measuring light beam enters the interface (reflecting surface) and the x-y plane is designated as an x axis. A y axis is designated such that the z axis and the x axis form a right hand coordinate system. Here, the coordinate origin is the center of the region of the detecting portion irradiated by the measuring light beam. However, the present invention is not limited to this configuration.

The "light transmitting space" is a space which is formed by the protective member and the light transmitting surface, and the term refers to a space that secures a transmission path of the measuring light beam as it enters the dielectric prism. Here, the term "first light transmitting space" refers to a light transmitting space that the measuring light beam passes through when it enters the sensor chip.

It is preferable for the first total reflection illuminated sensor chip of the present invention to be of a configuration, wherein the first protective member is of a tapered shape that causes the first light transmitting space to become larger toward the downward direction.

It is also preferable for the first protective member to be integrally formed with the dielectric prism. Alternatively, it is preferable for total reflection illuminated sensor chip of the present invention to further comprise: a lid member which is mounted above the dielectric prism; and for a configuration to be adopted, wherein: the first protective member is integrally formed with the lid member.

The first total reflection illuminated sensor chip of the present invention may further comprise: a second protective member, for protecting a second light transmitting surface of the dielectric prism, through which reflected light, which is the measuring light beam reflected at the interface, is output.

Here, the term "second" light transmitting surface refers to a surface of the dielectric prism through which reflected light, which is the measuring light beam reflected at the interface, is output.

It is preferable for the second protective member to be provided at a position which is a predetermined distance away from the second light transmitting surface so as to form a second light transmitting space, which is open at least toward the downward direction, between the second light transmitting surface and the second protective member; and for the total reflection illuminated sensor chip to be configured such that the reflected light that enters the second light transmitting space through the second light transmitting surface and passes beneath the second light transmitting space can be detected by a photodetector.

Here, the term "second light transmitting space" refers to a light transmitting space that the reflected light passes through when it exits the sensor chip.

It is preferable for the first total reflection illuminated sensor chip of the present invention to be of a configuration, wherein the second protective member is of a tapered shape that causes the second light transmitting space to become larger toward the downward direction.

It is also preferable for the second protective member to be integrally formed with the dielectric prism. Alternatively, it is preferable for total reflection illuminated sensor chip of the present invention to further comprise: a lid member which is mounted above the dielectric prism; and for a configuration to be adopted, wherein: the second protective member is integrally formed with the lid member.

The first total reflection illuminated sensor chip of the present invention may be of a configuration, wherein: a metal film is provided adjacent to the dielectric prism at the detecting portion; and the detecting method that the total reflection illuminated sensor chip is employed in utilizes an enhanced electric field caused by surface plasmon which is generated within the metal film due to the evanescent waves.

A second total reflection illuminated sensor chip of the present invention is employed in a detecting method for detecting a detection target substance comprising the steps of: supplying a sample that includes the detection target substance onto a detecting portion formed on a surface of a dielectric prism, irradiating a measuring light beam onto the interface between the dielectric prism and the detecting portion through a first light transmitting surface of the dielectric prism such that conditions for total reflection are satisfied at the interface, and utilizing evanescent waves which are generated at the detecting portion due to the irradiation of the measuring light beam to detect the detection target substance, and is characterized by comprising:

the dielectric prism;

the detecting portion formed on the surface of the dielectric prism; and a first protective member for protecting the first light transmitting surface;

the first protective member being provided so as to form a first light transmitting space having the shape of a cutout which is open at least toward the downward and forward directions and which communicates with the first light transmitting surface in the rearward direction; and the total reflection illuminated sensor chip being configured such that the interface can be irradiated by the measuring light beam that passes through the first light transmitting space and the first light transmitting surface.

Here, the "forward" and "rearward" directions refer to the positive direction and the negative direction along the x axis in the aforementioned coordinate system, respectively.

It is preferable for the first protective member to be integrally formed with the dielectric prism. Alternatively, it is preferable for total reflection illuminated sensor chip of the present invention to further comprise: a lid member which is mounted above the dielectric prism; and for a configuration to be adopted, wherein: the first protective member is integrally formed with the lid member.

The second total reflection illuminated sensor chip of the present invention may further comprise: a second protective member, for protecting a second light transmitting surface of the dielectric prism, through which reflected light, which is the measuring light beam reflected at the interface, is output.

It is preferable for the second total reflection illuminated sensor chip to be of a configuration, wherein: the second protective member is provided so as to form a second light transmitting space having the shape of a cutout which is open at least toward the downward and forward directions and which communicates with the second light transmitting surface in the rearward direction; and the total reflection illuminated sensor chip is configured such that the reflected light that passes through the second light transmitting surface and the second light transmitting space can be detected by a photodetector.

It is also preferable for the second protective member to be integrally formed with the dielectric prism. Alternatively, it is preferable for total reflection illuminated sensor chip of the present invention to further comprise: a lid member which is mounted above the dielectric prism; and for a configuration to be adopted, wherein: the second protective member is integrally formed with the lid member.

The second total reflection illuminated sensor chip of the present invention may be of a configuration, wherein: a metal film is provided adjacent to the dielectric prism at the detecting portion; and the detecting method that the total reflection illuminated sensor chip is employed in utilizes an enhanced electric field caused by surface plasmon which is generated within the metal film due to the evanescent waves.

The first and second total reflection illuminated sensor chips of the present invention are equipped with the protective members for protecting the surface, through which the measuring light beam enters the dielectric prism, or the surface, through which the reflected light is output from the dielectric prism, from damage and contamination, having simple structures and that secure transmission paths of the light. Accordingly, a total reflection illuminated sensor chip for use in a detecting method that detects detection target substances utilizing evanescent waves can be produced with a smaller number of parts and without complex molding steps for the protective members. Thereby, thin and low cost total reflection illuminated sensor chips can be realized.

BRIEF DESCRIPTION OF THE DRAWINGS

FIG. 10 is a diagram that illustrates the schematic structure of an SPR measuring apparatus that employs the sensor chip of the present invention.

DESCRIPTION OF THE PREFERRED EMBODIMENTS

Hereinafter, embodiments of the present invention will be described with reference to the attached drawings. However, the present invention is not limited to the embodiments to be described below.

Total Reflection Illuminated Sensor Chip

First Embodiment

Figure 1A:
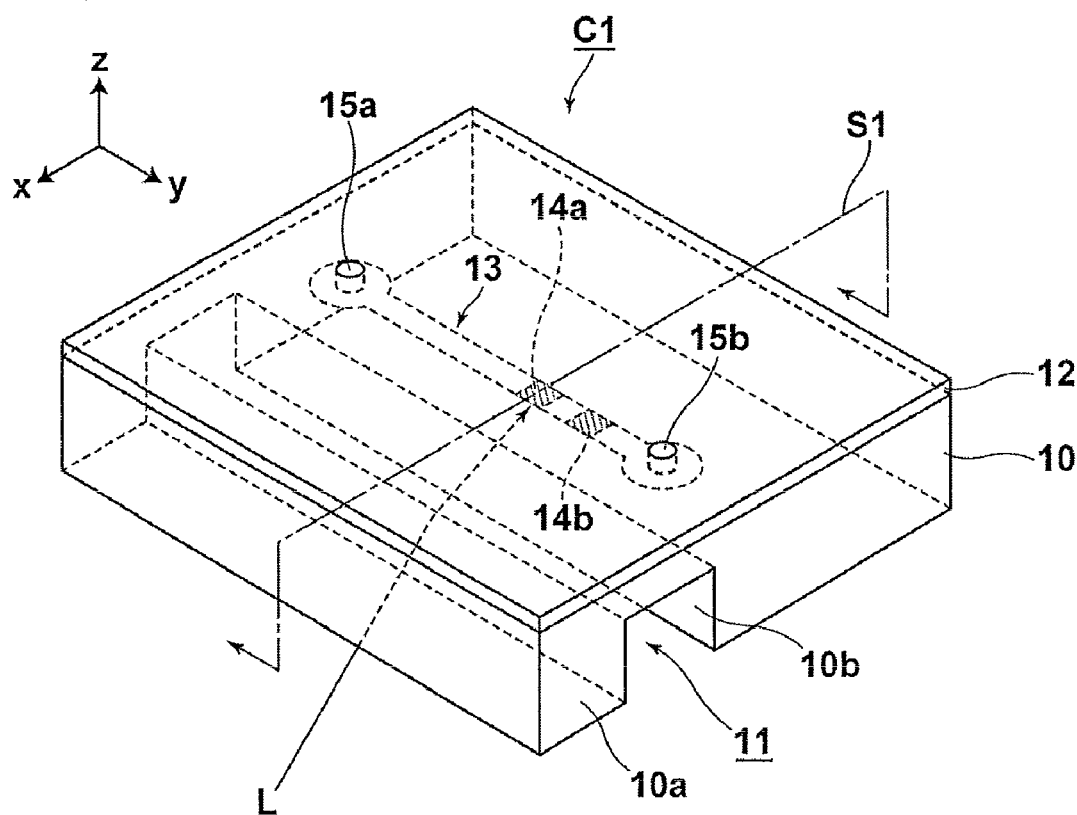
FIG. 1A is a schematic perspective view that illustrates a sensor chip according to a first embodiment of the present invention.
Figure 1B:
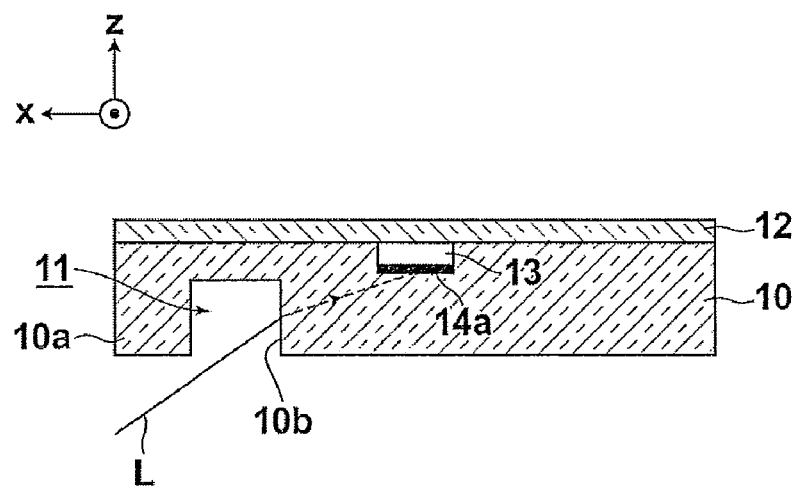
FIG. 1B is a schematic sectional view that illustrates the sensor chip of the first embodiment.

First, a total reflection illuminated sensor chip C1 according to a first embodiment of the present invention will be described. FIG. 1A is a schematic perspective view that illustrates the entirety of the structure of the sensor chip C1. FIG. 1B is a schematic sectional view of a z-x plane 51 that passes through a metal film 14a of the sensor chip C1. As illustrated in FIG. 1A and FIG. 1B, the coordinate system employed in the Figures has an x-y plane that includes the interface between a dielectric prism 10 and the metal film 14a, a direction perpendicular to the x-y plane and in which the metal film 14a is formed is designated as a z axis, and a direction which is opposite a direction in which projected components of a measuring light beam L travel toward a line of intersection between an incident surface (a plane which is perpendicular to the interface and includes incident light and reflected light) that the measuring light beam enters the interface (reflecting surface) and the x-y plane is designated as an x axis. A y axis is designated such that the z axis and the x axis form a right hand coordinate system. Hereinafter, the positive direction along the z axis will be referred to as the "upward direction", the negative direction along the z axis will be referred to as the "downward direction", the positive direction along the x axis will be referred to as the "forward direction", and the negative direction along the x axis will be referred to as the "rearward direction" in this coordinate system.

As illustrated in FIG. 1A and FIG. 1B, the sensor chip C1 is equipped with: a dielectric prism 10 having a first protective member 10a formed integrally therewith and also having a flow channel 13 which is open toward the upward direction and which has metal films 14a and 14b formed at predetermined regions; and a lid member 12 which is mounted on the dielectric prism 10 to form an upper surface of the flow channel 13. The sensor chip C1 is utilized for SPFS measurement or SPR measurement.

The dielectric prism 10 is equipped with the flow channel 13, through which samples that include detection target substances and the like are caused to flow through. The first protective member 10a is integrally formed with the dielectric prism 10. In addition, the dielectric prism 10 is also equipped with a first light transmitting surface 10b (the surface of the dielectric prism through which a measuring light beam enters the dielectric prism), which is parallel to a y-z plane and is protected by the first protective member 10a. The first light transmitting surface 10b is not necessarily parallel to the y-z plane. As illustrated in FIG. 1B, the sensor chip C1 is configured such that the interface between the dielectric prism 10 and the metal film 14a can be irradiated by the measuring light beam L that enters a first light transmitting space 11 from below the first light transmitting space 11 and passes through the first light transmitting surface 10b, such that conditions for total reflection are satisfied at the interface. The material of the dielectric prism 10 is a transparent material, such as a transparent resin or glass. It is desirable for the dielectric prism 10 to be formed by resin. In the case that the dielectric prism 10 is formed by resin, polymethyl methacrylate (PMMA), polycarbonate (PC), and non crystalline polyolefin (APO) that includes cycloolefin may be favorably employed.

The first protective member 10a is provided at a position which is a predetermined distance away from the first light transmitting surface 10b so as to form the first light transmitting space 11, which is open at least toward the downward direction, between the first light transmitting surface 10b and the first protective member 10a. In the first embodiment, the first protective member 10a is formed integrally with the dielectric prism 10, as illustrated in FIG. 1A and FIG. 1B. In addition, the first light transmitting space 11 is open along the y axis (the positive direction and negative direction along the y axis), in addition to being open toward the downward direction. The distance between the first protective member 10a and the first light transmitting surface 10b, that is, the length of the first light transmitting space 11 in the direction along the x axis, is not particularly limited. This distance may be determined as appropriate within a range that enables the first protective member 10a to protect the first light transmitting surface 10b, while not interfering with the measuring light beam L entering the first light transmitting surface 10b.

The flow channel 13 is formed by a U shaped groove formed in the dielectric prism 10 and the lid member 12, which is mounted on the dielectric prism 10. Further, liquid reservoirs for injecting liquids or discharging liquids are formed at the ends of the flow channel 13. In addition, the metal films 14a and 14b that function as detecting portions are formed at predetermined regions within the flow channel 13. In the first embodiment, the metal film 14a is employed as a measurement detecting portion, and the metal film 14b is employed as a reference detecting portion. However, the reference detecting portion is not necessary, as long as one measurement detecting portion is provided. The material of the metal films 14a and 14b is not particularly limited.

Examples of materials which are desirable from the viewpoint of inducing plasmon include Au, Ag, Cu, Pt, Ni, and Ti. Among these, Au and Ag, which exhibit high electric field enhancing effects, are particularly preferred. It is desirable for the thicknesses of the metal films 14a and 14b to be determined such that surface plasmon is strongly excited, taking the material of the metal films 14a and 14b and the wavelength of the measuring light beam L into consideration. For example, in the case that a laser beam having a central wavelength of 780 nm is employed as the measuring light beam L, and Au is employed as the material of the metal films 14a and 14b, a favorable thickness of the metal layer 12a is 50 nm±5 nm.

The lid member 12 forms the upper surface of the flow channel 13 by being mounted on the dielectric prism 10. An injection opening 15a, through which samples and the like are injected into the injection reservoir, and an air aperture 15b, through which air and the like are drawn out, that communicates with the liquid discharge reservoir, are formed in the lid member 12. The same materials listed previously as materials for the dielectric prism 10 may be employed as the material of the lid member 12.

As described above, the sensor chip C1 of the first embodiment is equipped with the protective member 10a for protecting the first light transmitting surface 10b from damage and contamination, having a simple structure and that forms the light transmitting space 11 to secure a transmission path for light. The first protective member 10a, which is integrally formed with the dielectric prism 10, is of a structure that can be formed by common a molding method (injection molding or optical molding, for example). Further, there are only two parts of the sensor chip C1 of the first embodiment, that is, the dielectric prism 10 and the lid member 12. Accordingly, a total reflection illuminated sensor chip for use in a detecting method that detects detection target substances utilizing evanescent waves can be produced with a smaller number of parts and without complex molding steps for the protective members. Thereby, thin and low cost total reflection illuminated sensor chips can be realized.

Design Modifications to the First Embodiment

Figure 2A:
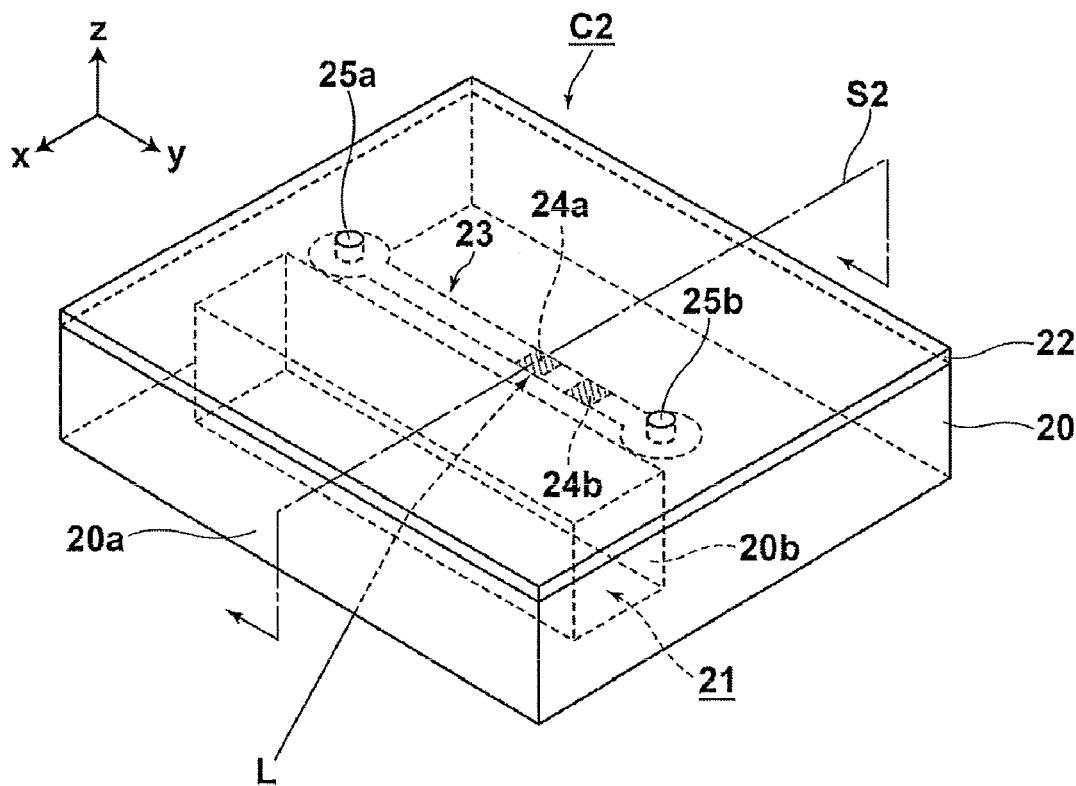
FIG. 2A is a schematic perspective view that illustrates a sensor chip according to a first modified design of the first embodiment.
Figure 2B:
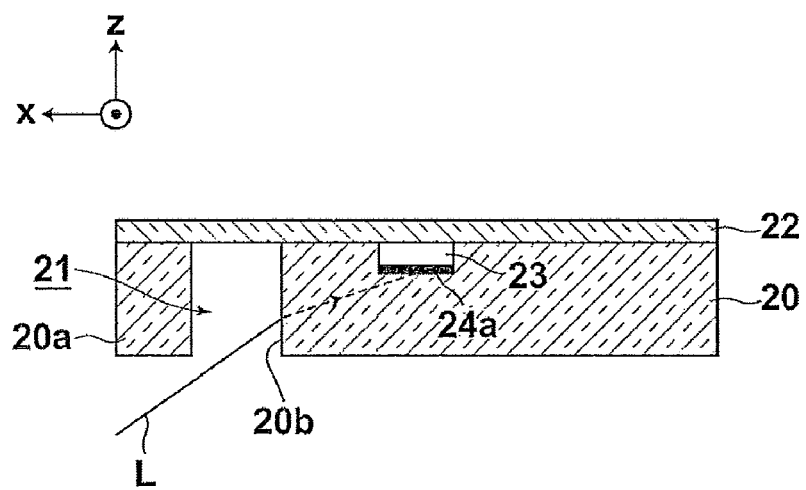
FIG. 2B is a schematic sectional view that illustrates the sensor chip according to the first modified design of the first embodiment.

The sensor chip C1 of the first embodiment has been described as a case in which the first light transmitting space 11 is open in the downward direction and in the directions along the y axis. Alternatively, a first light transmitting space 21 may be configured such that it is only open toward the downward direction, as in the total reflection illuminated sensor chip C2 illustrated in FIG. 2A and FIG. 2B. The first light transmitting space 21 may be open in the upward direction within a dielectric prism 20, that is, may be open up to a lid member 22.

Figure 3A:
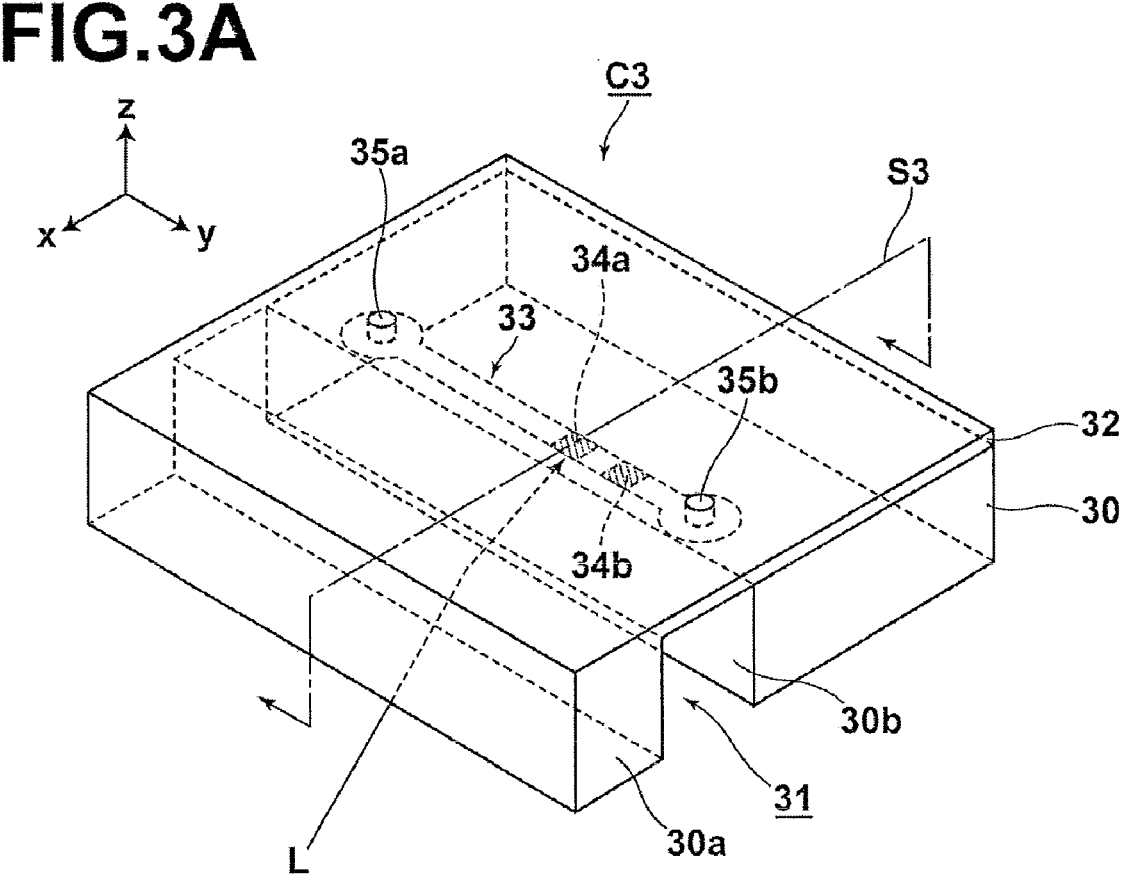
FIG. 3A is a schematic perspective view that illustrates a sensor chip according to a second modified design of the first embodiment.
Figure 3B:
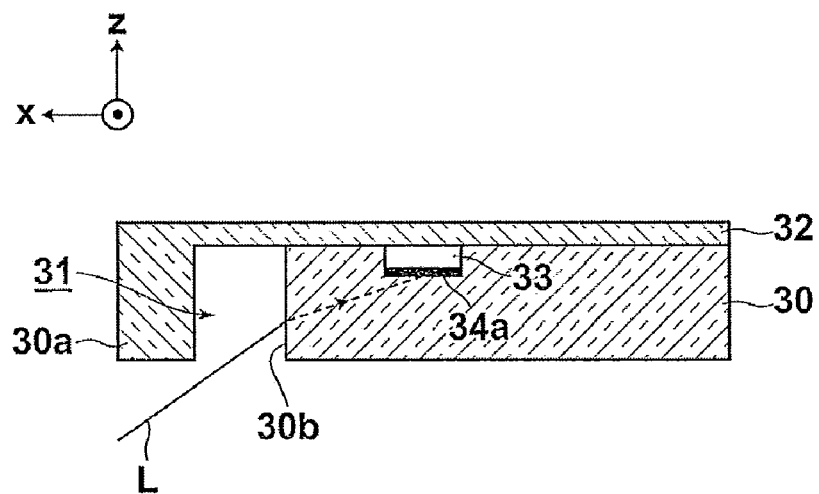
FIG. 3B is a schematic sectional view that illustrates the sensor chip according to the second modified design of the first embodiment.

In addition, the sensor chip C1 of the first embodiment has been described as a case in which the first protective member 10a is integrally formed with the dielectric prism 10. Alternatively, a first protective member 30a may be integrally formed with a lid member 32, as in the total reflection illuminated sensor chip C3 illustrated in FIG. 3A and FIG. 3B.

Further, the first protective member is of an L shape in the examples described above. That is, cases have been described in which a portion of the first protective member faces frontward toward the first light transmitting surface. However, the first protective member is not limited to this configuration. That is, the first protective member may be of an I shape, in which the forward portion of the aforementioned L shape is open toward the front. Even if this configuration is adopted, the objective of the present invention can be achieved. In this case, the light transmitting space becomes a space sandwiched between the I shaped protective member, the tip of which is a predetermined distance away from the light transmitting surface, and the light transmitting surface.

The same advantageous effects as those obtained by the first embodiment described above can be obtained, in cases that the three design modifications above are adopted.

Second Embodiment

Figure 4A:
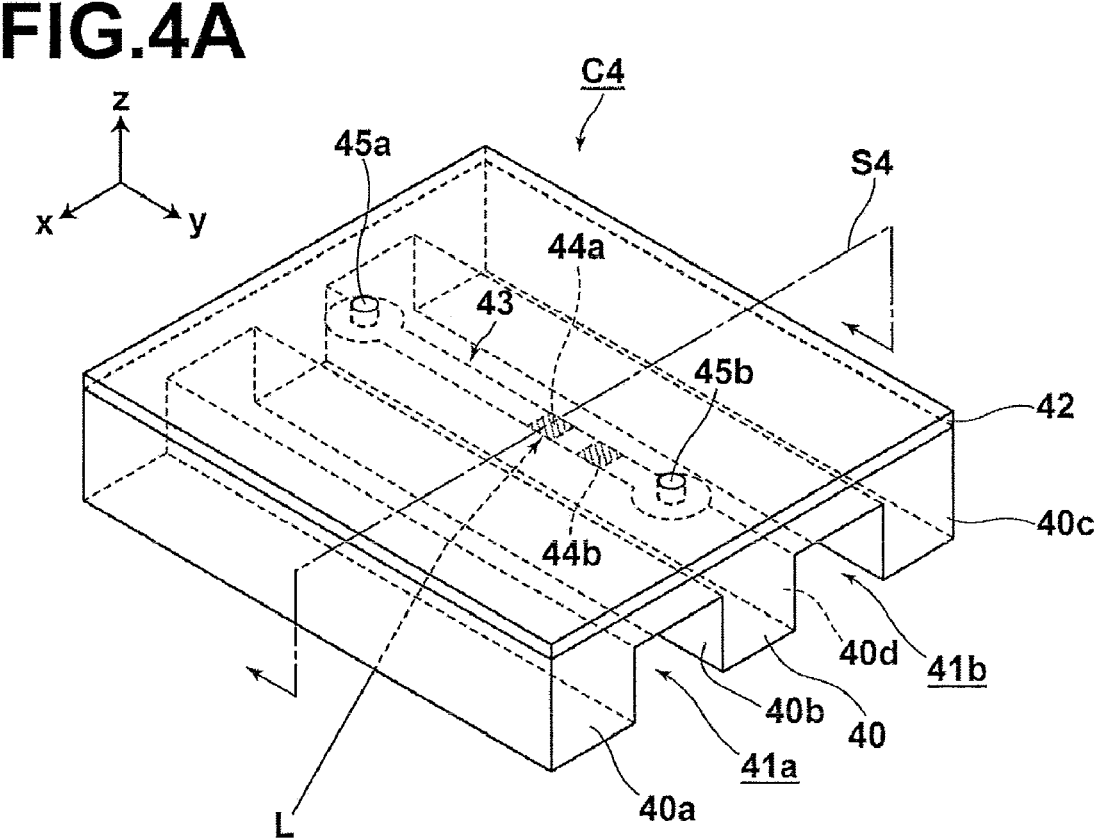
FIG. 4A is a schematic perspective view that illustrates a sensor chip according to a second embodiment of the present invention.
Figure 4B:
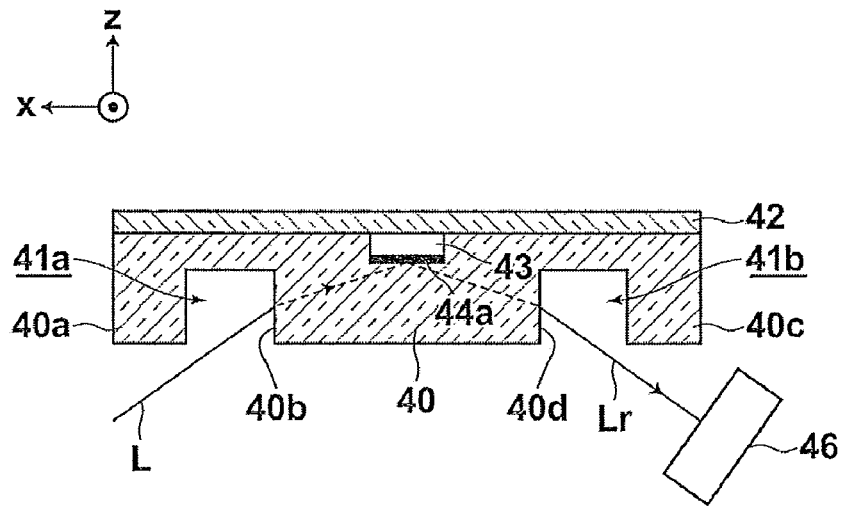
FIG. 4B is a schematic sectional view that illustrates the sensor chip of the second embodiment.

First, a total reflection illuminated sensor chip C4 according to a second embodiment of the present invention will be described. FIG. 4A is a schematic perspective view that illustrates the entirety of the structure of the sensor chip C4. FIG. 4B is a schematic sectional view of a z-x plane S4 that passes through a metal film 44a of the sensor chip C4. The construction of the sensor chip C4 is similar to that of the sensor chip C1 of the first embodiment. However, the sensor chip C4 differs from the sensor chip C1 in that it has a second light transmitting surface 40d (the surface of the dielectric prism through which reflected light exits the dielectric prism), and a second protective member 40c that protects the second light transmitting surface 40d. Accordingly, descriptions of constituent elements which are the same as those of the sensor chip C1 will be omitted insofar as they are not particularly necessary. The sensor chip C4 is also utilized to perform SPFS measurement or SPR measurement. The sensor chip C4 has the second protective member 40c that protects the second light transmitting surface 40d. Thereby, reflected light Lr, which is the measuring light beam L reflected at the interface between a dielectric prism 40 and the metal film 44a can be more accurately detected. Accordingly, the sensor chip C4 is more favorable for use as a sensor chip for SPR measurement than the sensor chip C1.

As illustrated in FIG. 4A and FIG. 4B, the sensor chip C4 is equipped with: a dielectric prism 40 having a first protective member 40a and a second protective member 40c formed integrally therewith and also having a flow channel 43 which is open toward the upward direction and which has metal films 44a and 44b formed at predetermined regions; and a lid member 42 which is mounted on the dielectric prism 40 to form an upper surface of the flow channel 43.

The dielectric prism 40 is equipped with the flow channel 43, through which samples that include detection target substances and the like are caused to flow through. The first protective member 40a and the second protective member 40b are integrally formed with the dielectric prism 40. In addition, the dielectric prism 40 is also equipped with a first light transmitting surface 40b, which is parallel to a y-z plane and is protected by the first protective member 40a, and the second light transmitting surface 40d, which is parallel to a y-z plane and is protected by the second protective member 40b. The first light transmitting surface 40b and the second light transmitting surface 40d are not necessarily parallel to the y-z plane. As illustrated in FIG. 4B, the sensor chip C4 is configured such that the interface between the dielectric prism 40 and the metal film 44a can be irradiated by a measuring light beam L that enters a first light transmitting space 41b from below the first light transmitting space 41b and passes through the first light transmitting surface 40b, such that conditions for total reflection are satisfied at the interface. Further, the sensor chip C4 is configured such that reflected light Lr, which is the measuring light beam L reflected at the interface, that enters a second light transmitting space 41b through the second light transmitting surface 40d and passes beneath the second light transmitting space 41b can be detected by a photodetector 46. Materials similar to those employed for the dielectric prism 10 of the first embodiment may be employed for the dielectric prism 40.

The second protective member 40c is provided at a position which is a predetermined distance away from the second light transmitting surface 40d so as to form the second light transmitting space 41b, which is open at least toward the downward direction, between the second light transmitting surface 41b and the second protective member 40c. In the second embodiment, the second protective member 40c is formed integrally with the dielectric prism 40 in the same manner as the first protective member 40a, as illustrated in FIG. 4A and FIG. 4B. In addition, the second light transmitting space 41b is open in the directions along the y axis, in addition to being open toward the downward direction. The distance between the second protective member 40c and the second light transmitting surface 40d, that is, the length of the second light transmitting space 41b in the direction along the x axis, is not particularly limited. This distance may be determined as appropriate within a range that enables the second protective member 40c to protect the second light transmitting surface 40d, while not interfering with the reflected light beam Lr being output through the second light transmitting surface 40d.

As described above, the sensor chip C4 of the second embodiment is equipped with the protective member 40a and the protective member 40c for protecting the first light transmitting surface 40b and the second light transmitting surface 40d from damage and contamination, having a simple structure and that forms the light transmitting space 41a and the light transmitting space 41b to secure transmission paths for light. Accordingly, the same advantageous effects as those obtained by the sensor chip C1 of the first embodiment can be obtained.

Further, the sensor chip C4 of the second embodiment is provided with the second light transmitting surface 40d. Thereby, detection of the reflected light Lr is facilitated. Accordingly, the sensor chip C4 of the second embodiment is a favorable sensor chip, particularly for use in SPR measurement.

Design Modifications to the Second Embodiment

The sensor chip C4 of the second embodiment is not limited to that in which the first protective member and the second protective member are of the same type. That is, one of the two protective members may be of a tapered shape. Alternatively, one of the protective members may be provided at a position which is a predetermined distance away from one of the light transmitting surfaces so as to form a light transmitting space, which is open at least toward the downward direction, while the other of the protective members is provided so as to form a light transmitting space having the shape of a cutout which is open at least toward the downward and forward directions and which communicates with the other light transmitting surface in the rearward direction. However, it is preferable for the two protective members to be of the same type, from the viewpoint of manufacturing costs. The above also applies to the fifth embodiment, which will be described later.

Further, the first protective member and the second protective member are of an L shape in the examples described above. That is, cases have been described in which a portion of the first protective member faces frontward toward the first light transmitting surface, and a portion of the second protective member faces frontward toward the second light transmitting surface. However, the first protective member and the second protective member are not limited to this configuration. That is, the first protective member and the second protective member may be of an I shape, in which the forward portion of the aforementioned L shape is open toward the front. Alternatively, only one of the first protective member and the second protective member may be of the I shape. Even if this configuration is adopted, the objective of the present invention can be achieved. In this case, the light transmitting space becomes a space sandwiched between the I shaped protective member, the tip of which is a predetermined distance away from the light transmitting surface, and the light transmitting surface.

Third Embodiment

Figure 5A:
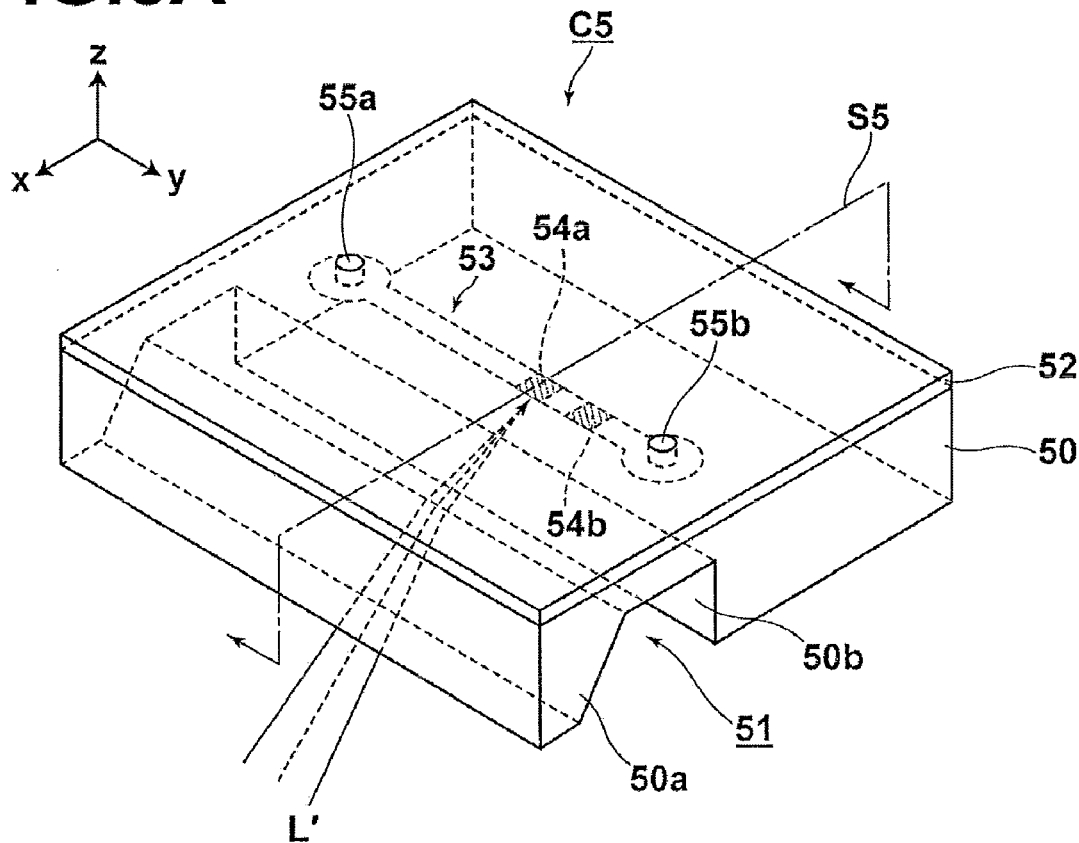
FIG. 5A is a schematic perspective view that illustrates a sensor chip according to a third embodiment of the present invention.
Figure 5B:
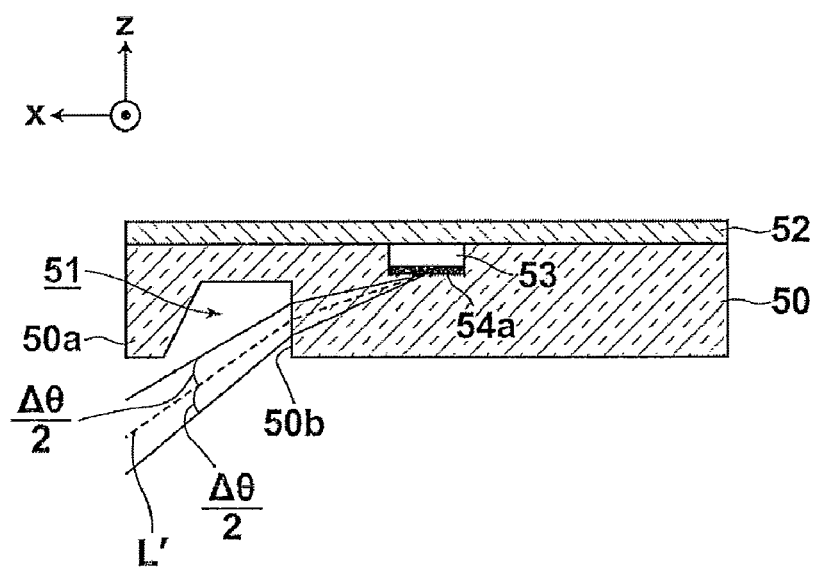
FIG. 5B is a schematic sectional view that illustrates the sensor chip of the third embodiment.

First, a total reflection illuminated sensor chip C5 according to a second embodiment of the present invention will be described. FIG. 5A is a schematic perspective view that illustrates the entirety of the structure of the sensor chip C5. FIG. 5B is a schematic sectional view of a z-x plane S5 that passes through a metal film 54a of the sensor chip C4. The construction of the sensor chip C5 is similar to that of the sensor chip C1 of the first embodiment. However, the sensor chip C5 differs from the sensor chip C1 in that it has a first protective member 50a of a tapered shape that cause a first light transmitting space 51 to become larger in the downward direction. Accordingly, descriptions of constituent elements which are the same as those of the sensor chip C1 will be omitted insofar as they are not particularly necessary. The sensor chip C5 is also utilized to perform SPFS measurement or SPR measurement. The sensor chip C5 is equipped with the first protective member 50a having the tapered shape, such that entrance of a fan beam (converging light beam) L' having an angular width Δθ into a dielectric prism 50 is not blocked. Accordingly, the sensor chip C5 is more favorable for use as a sensor chip in the case that the fan beam L' is employed as a measuring light beam than the sensor chip C1.

As illustrated in FIG. 5A and FIG. 5B, the sensor chip C5 is equipped with: the dielectric prism 50 having the first protective member 50a formed integrally therewith and also having a flow channel 53 which is open toward the upward direction and which has metal films 54a and 54b formed at predetermined regions; and a lid member 52 which is mounted on the dielectric prism 50 to form an upper surface of the flow channel 53.

The first protective member 50a is provided at a position which is a predetermined distance away from a first light transmitting surface 50b so as to form the first light transmitting space 51, which is open at least toward the downward direction, between the first light transmitting surface 50b and the first protective member 50a. In the third embodiment, the first protective member 50a is formed integrally with the dielectric prism 50, as illustrated in FIG. 5A and FIG. 5B. In addition, the first light transmitting space 51 is open along the y axis, in addition to being open toward the downward direction. Further, the first protective member 50a is of a tapered shape that causes the first light transmitting space 51 to become larger in the downward direction. Thereby, the sensor chip C5 is more favorable for use as a sensor chip in the case that the fan beam (converging light beam) L' having an angular width A0 is employed as the measuring light beam. The degree of spread of the first light transmitting space 51 depends on the tapered shape, and is not particularly limited. The degree of spread may be determined as appropriate within a range that enables the first protective member 50a to protect the first light transmitting surface 50b, while not interfering with the entrance of the fan beam L' into the first light transmitting surface 50b.

As described above, the sensor chip C5 of the third embodiment is equipped with the first protective member 50a for protecting the first light transmitting surface 50b from damage and contamination, having a simple structure and that forms the light transmitting space 51a to secure a transmission path for light. Accordingly, the same advantageous effects as those obtained by the sensor chip C1 of the first embodiment can be obtained.

Further, the first protective member 50a of the third embodiment is of a tapered shape that causes the first light transmitting space 51 to become larger toward the downward direction. Accordingly, portions that block entrance of measuring light beams having angular widths are reduced in the sensor chip C5 of the third embodiment, and the sensor chip C5 is favorable for use as a sensor chip in the case that the fan beam L' is employed as the measuring light beam.

Design Modifications to the Third Embodiment

A case has been described in which the sensor chip C5 of the third embodiment is equipped only with the first light transmitting space 51 and the first protective member 50a. However, the sensor chip C5 may be further equipped with a second protective member of a shape similar to that of the first protective member 50a, as in the sensor chip C4 of the second embodiment. By adopting such a configuration, the sensor chip C5 will become favorable for use as a sensor chip in the case that the fan beam L' is employed as the measuring light beam to perform SPR measurement.

Fourth Embodiment

Figure 6A:
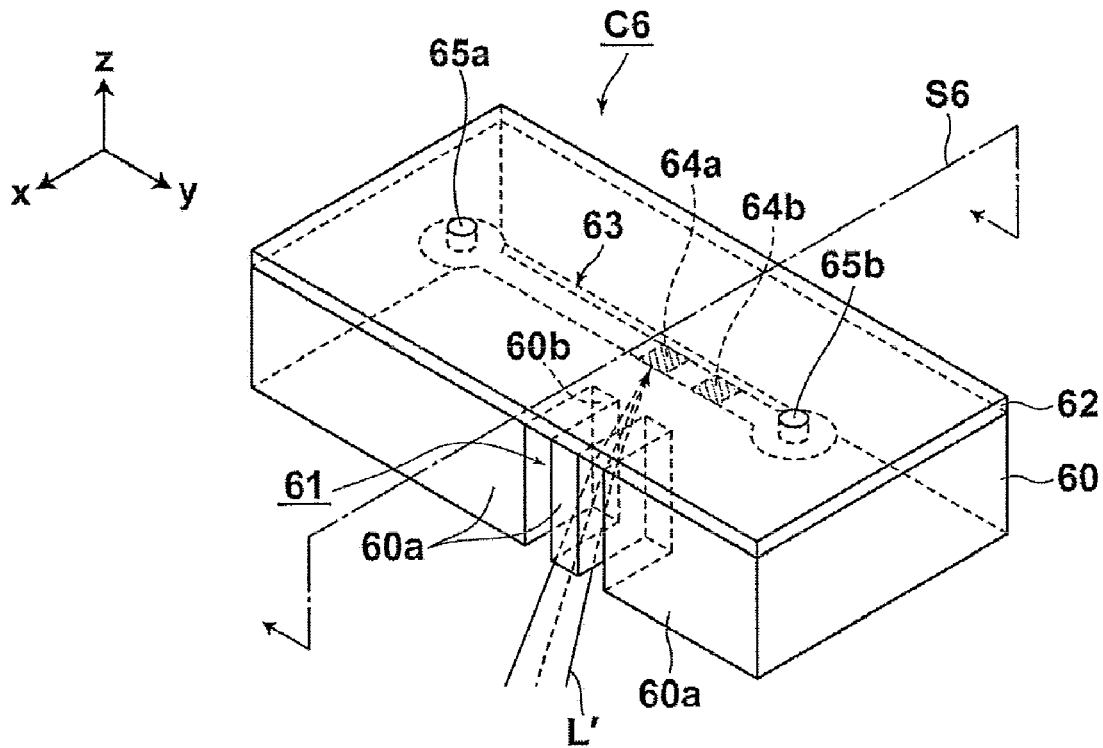
FIG. 6A is a schematic perspective view that illustrates a sensor chip according to a fourth embodiment of the present invention.
Figure 6B:
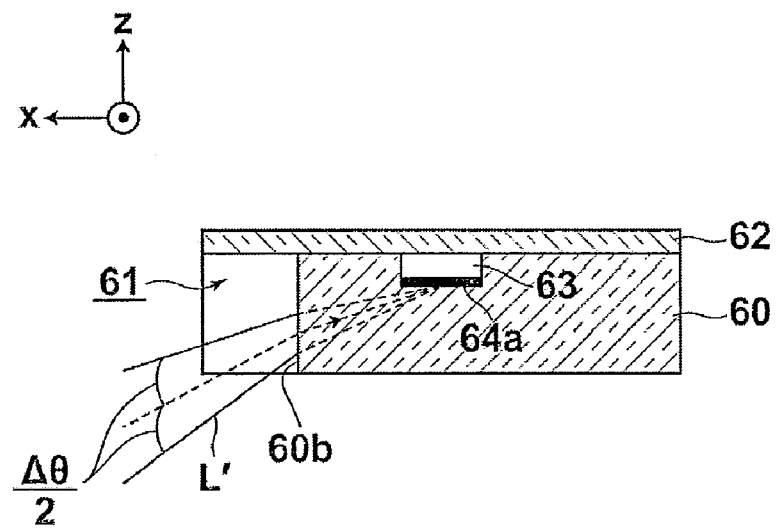
FIG. 6B is a schematic sectional view that illustrates the sensor chip of the fourth embodiment.

First, a total reflection illuminated sensor chip C6 according to a fourth embodiment of the present invention will be described. FIG. 6A is a schematic perspective view that illustrates the entirety of the structure of the sensor chip C6. FIG. 6B is a schematic sectional view of a z-x plane S6 that passes through a metal film 64a of the sensor chip C6.

As illustrated in FIG. 6A and FIG. 6B, the sensor chip C6 is equipped with: a dielectric prism 60 having a first protective member 60a formed integrally therewith and also having a flow channel 63 which is open toward the upward direction and which has metal films 64a and 64b formed at predetermined regions; and a lid member 62 which is mounted on the dielectric prism 60 to form an upper surface of the flow channel 63. The sensor chip C6 is also utilized to perform SPFS measurement or SPR measurement, for example. The sensor chip C6 is equipped with the first protective member 60a that forms spaces in the shapes of cutouts. Thereby, entrance of a fan beam L' having an angular width Δθ into the dielectric prism 60 is not blocked. Accordingly, the sensor chip C6 is more favorable for use as a sensor chip in the case that the fan beam L' is employed as a measuring light beam than the sensor chip C1.

The dielectric prism 60 is equipped with the flow channel 63, through which samples that include detection target substances and the like are caused to flow through. The first protective member 60a is integrally formed with the dielectric prism 60. In addition, the dielectric prism 40 is also equipped with a first light transmitting surface 60b, which is parallel to a y-z plane and is protected by the first protective member 60a. The first light transmitting surface 60b is not necessarily parallel to the y-z plane. As illustrated in FIG. 6B, the sensor chip C6 is configured such that the interface between the dielectric prism 60 and the metal film 64a can be irradiated by the fan beam L' that enters a first light transmitting space 61 from below or from in front of the first light transmitting space 61 and passes through the first light transmitting surface 60*b*, such that conditions for total reflection are satisfied at the interface. Materials similar to those employed for the dielectric prism 10 of the first embodiment may be employed for the dielectric prism 60.

The first protective member 60*a* is provided so as to form the first light transmitting space 61, which is open at least in the downward and forward directions, and which communicates with the first light transmitting surface 60*b* in the rearward direction. Alternatively, as illustrated in FIG. 6A and FIG. 6B, first light transmitting spaces 61 may be formed by pairs of surfaces of the first protective member 60*a*, which is formed integrally with the dielectric prism 60, that face each other, and the lid member 62. The distance between the surfaces of the first protective member 60*a* that face each other, that is, the length of each of the first light transmitting spaces 61 in the direction along the y axis, is not particularly limited. This distance may be determined as appropriate within a range that enables the first protective member 60*a* to protect the first light transmitting surface 60*b*, while not interfering with the entrance of the fan beam L' into the first light transmitting surface 60*b*. Note that two first light transmitting spaces 61 are formed in the sensor chip C6 of the fourth embodiment. One of the two first light transmitting spaces 61 is provided such that the fan beam L' is enabled to be irradiated onto the metal film 64*a* of a measurement detecting portion, and the other is provided such that the fan beam L' is enabled to be irradiated onto the metal film 64*b* of a reference detecting portion. Here, the number of first light transmitting spaces 61 is not particularly limited, and may be selected as appropriate according to the number of detecting portions, the manner in which measurement is performed, and the like.

The flow channel 63 and the lid member 62 of the sensor chip C6 of the fourth embodiment are the same as the flow channel 13 and the lid member 12 of the sensor chip C1 of the first embodiment.

As described above, the sensor chip C6 of the fourth embodiment is equipped with the protective member 60*a* for protecting the first light transmitting surface 60*b* from damage and contamination, having a simple structure and that forms the light transmitting space 61 to secure a transmission path for light. The first protective member 60*a*, which is integrally formed with the dielectric prism 60, is of a structure that can be formed by common a molding method (injection molding or optical molding, for example). Further, there are only two parts of the sensor chip C6 of the fourth embodiment, that is, the dielectric prism 60 and the lid member 62. Accordingly, the same advantageous effects as those obtained by the sensor chip C1 of the first embodiment can be obtained.

Further, in the sensor chip C6 of the fourth embodiment, the first light transmitting spaces 61 are formed as cutouts in the dielectric prism 60. Thereby, there is a degree of allowance in the heights of the first light transmitting spaces, that is, the lengths of the first light transmitting spaces 61 in the direction along the z axis. Accordingly, portions that block entrance of measuring light beams having angular widths are further reduced, and the sensor chip C6 is favorable for use as a sensor chip in the case that the fan beam L' is employed as the measuring light beam.

Fifth Embodiment

Figure 7A:
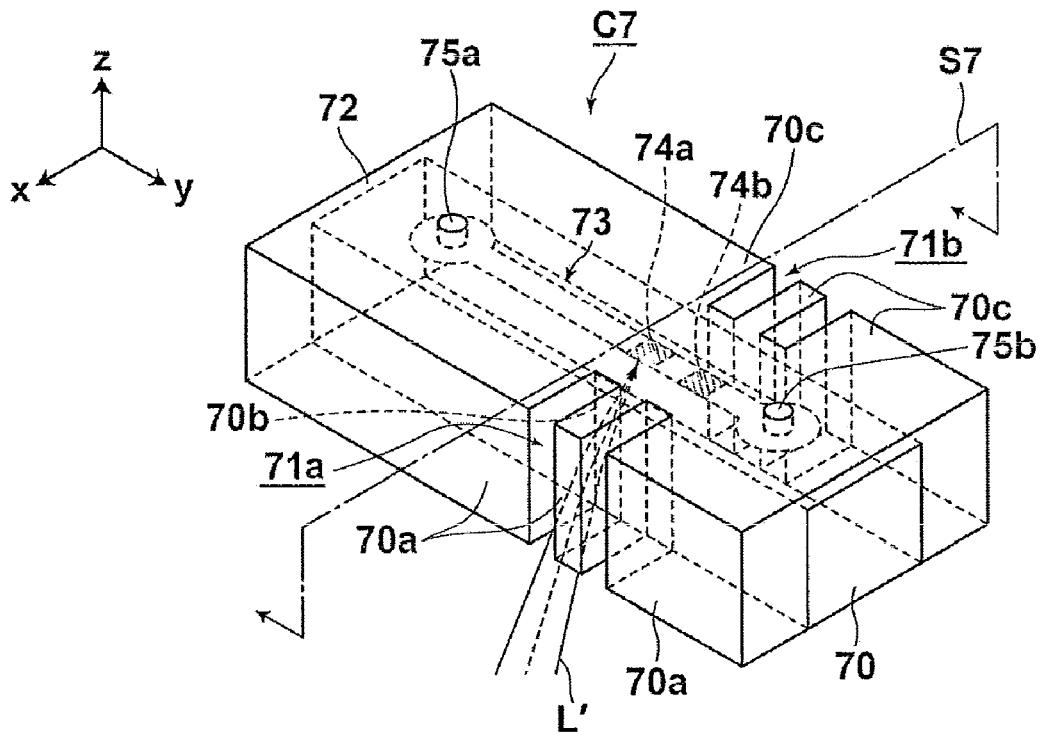
FIG. 7A is a schematic perspective view that illustrates a sensor chip according to a fifth embodiment of the present invention.
Figure 7B:
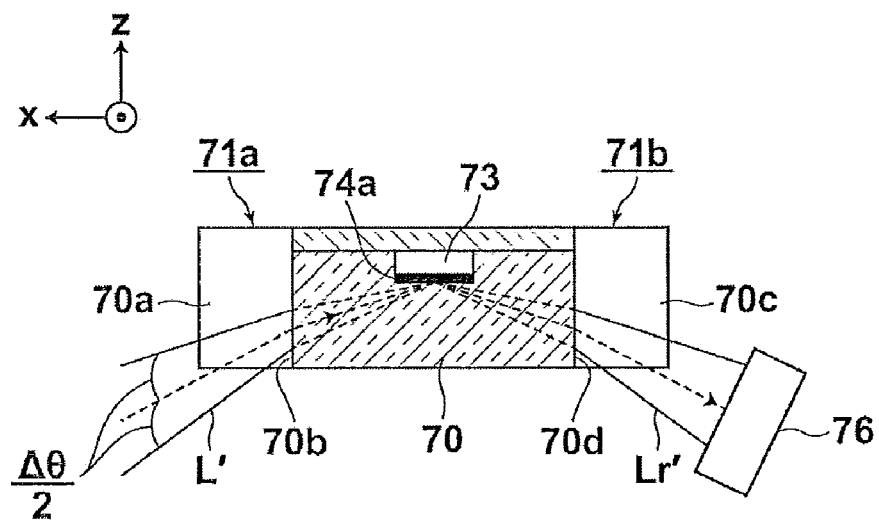
FIG. 7B is a schematic sectional view that illustrates the sensor chip of the fifth embodiment.

First, a total reflection illuminated sensor chip C7 according to a fifth embodiment of the present invention will be described. FIG. 7A is a schematic perspective view that illustrates the entirety of the structure of the sensor chip C7. FIG. 7B is a schematic sectional view of a z-x plane S7 that passes through a metal film 74*a* of the sensor chip C7.

As illustrated in FIG. 7A and FIG. 7B, the sensor chip C7 is equipped with: a dielectric prism 70 having a flow channel 73 which is open toward the upward direction and which has metal films 74*a* and 74*b* formed at predetermined regions; and a lid member 72 which is mounted on the dielectric prism 70 to form an upper surface of the flow channel 73, having a first protective member 70*a* and a second protective member 70*c* formed integrally therewith. The sensor chip C7 is also utilized to perform SPFS measurement or SPR measurement, for example. The sensor chip C7 has the second protective member 70*c* that protects a second light transmitting surface 70*d*. Thereby, reflected light Lr, which is the measuring light beam L reflected at the interface between the dielectric prism and the metal film 74*a* can be more accurately detected. Accordingly, the sensor chip C7 is more favorable for use as a sensor chip for SPR measurement than the sensor chip C6.

The dielectric prism 70 is equipped with the flow channel 73, through which samples that include detection target substances and the like are caused to flow through. In addition, the dielectric prism 70 is also equipped with a first light transmitting surface 70*b*, which is parallel to a y-z plane and is protected by the first protective member 70*a*, and the second light transmitting surface 70*d*, which is parallel to a y-z plane and is protected by the second protective member 70*c*. The first light transmitting surface 70*b* and the second light transmitting surface 70*d* are not necessarily parallel to the y-z plane. Materials similar to those employed for the dielectric prism 10 of the first embodiment may be employed for the dielectric prism 70.

The first protective member 70*a* is provided so as to form the first light transmitting space 71*a*, which is open at least in the downward and forward directions, and which communicates with the first light transmitting surface 70*b* in the rearward direction. Alternatively, as illustrated in FIG. 7A and FIG. 7B, first light transmitting spaces 71*a* may be formed by pairs of surfaces of the first protective member 70*a*, which is formed integrally with the lid member 72, that face each other, and the first light transmitting surface 70*b*. Accordingly, in the fifth embodiment, the first light transmitting spaces 71*a* are open toward the downward direction, the forward direction, and the positive direction along the z axis. As illustrated in FIG. 7A and FIG. 7B, the first protective member 70*a* is formed integrally with the lid member 72. The distance between the surfaces of the first protective member 70*a* that face each other, that is, the length of each of the first light transmitting spaces 71*a* in the direction along the y axis, is not particularly limited. This distance may be determined as appropriate within a range that enables the first protective member 70*a* to protect the first light transmitting surface 70*b*, while not interfering with the entrance of the fan beam L' into the first light transmitting surface 70*b*. Note that two first light transmitting spaces 71*a* are formed in the sensor chip C7 of the fifth embodiment. One of the two first light transmitting spaces 71*a* is provided such that the fan beam L' is enabled to be irradiated onto the metal film 74*a* of a measurement detecting portion, and the other is provided such that the fan beam L' is enabled to be irradiated onto the metal film 74*b* of a reference detecting portion. Here, the number of first light transmitting spaces 71*a* is not particularly limited, and may be selected as appropriate according to the number of detecting portions, the manner in which measurement is performed, and the like.

The second protective member 70*c* is provided so as to form a second light transmitting space 71*b*, which is open at least in the downward and rearward directions, and which communicates with the second light transmitting surface 70d in the forward direction. Alternatively, as illustrated in FIG. 7A and FIG. 7B, second light transmitting spaces 71b may be formed by pairs of surfaces of the second protective member 70c, which is formed integrally with the lid member 72, that face each other, and the second light transmitting surface 70d. Accordingly, in the fifth embodiment, the second light transmitting spaces 71b are open toward the downward direction, the rearward direction, and the positive direction along the z axis. As illustrated in FIG. 7A and FIG. 7B, the second protective member 70c is formed integrally with the lid member 72. The distance between the surfaces of the second protective member 70c that face each other, that is, the length of each of the second light transmitting spaces 71b in the direction along the y axis, is not particularly limited. This distance may be determined as appropriate within a range that enables the second protective member 70c to protect the second light transmitting surface 70d, while not interfering with the reflected light Lr', which is the fan beam L' reflected at the interface between the metal films 74a and 74b and the dielectric prism 70, being output through the second light transmitting surface 70d. Note that two second light transmitting spaces 71b are formed in the sensor chip C7 of the fifth embodiment. One of the two second light transmitting spaces 71b is provided such that reflected light Lr', which is the fan beam L' reflected at the metal film 74a of the measurement detecting portion can propagate therethrough, and the other is provided such that reflected light Lr', which is the fan beam L' reflected at the metal film 74b of the reference detecting portion can propagate therethrough. Here, the number of second light transmitting spaces 71b is not particularly limited, and may be selected as appropriate according to the number of detecting portions, the manner in which measurement is performed, and the like.

The flow channel 73 is the same as the flow channel 13 of the first embodiment.

The lid member 72 forms the upper surface of the flow channel 73 by being mounted on the dielectric prism 70. An injection opening 75a, through which samples and the like are injected into an injection reservoir, and an air aperture 75b, through which air and the like are drawn out, that communicates with a liquid discharge reservoir, are formed in the lid member 72. The same materials listed previously as materials for the dielectric prism 70 may be employed as the material of the lid member 72. The lid member 72 is also equipped with the first protective member 70a and the second protective member 70c formed integrally therewith. As illustrated in FIG. 7B, the lid member 72 is configured such that the interface between the dielectric prism 70 and the metal film 74a can be irradiated by the fan beam L' that enters the first light transmitting space 71a from below and/or from in front of the first light transmitting space 71a and passes through the first light transmitting surface 70b, such that conditions for total reflection are satisfied at the interface. Further, as illustrated in FIG. 7B, the lid member 72 is configured such that reflected light Lr', which is the fan beam L' reflected at the interface, that enters the second light transmitting space 71b through the second light transmitting surface 70d and passes beneath and/or behind the second light transmitting space 71b can be detected by a photodetector 76.

As described above, the sensor chip C7 of the fifth embodiment is equipped with the protective member 70a and the protective member 70c for protecting the first light transmitting surface 70b and the second light transmitting surface 70d from damage and contamination, having simple structures and that form the light transmitting space 71a and the light transmitting space 71b to secure transmission paths for light. Accordingly, the same advantageous effects as those obtained by the sensor chip C1 of the first embodiment can be obtained.

In addition, in the sensor chip C7 of the fifth embodiment, the first light transmitting spaces 71a and the second light transmitting spaces 71b are formed as cutouts in the dielectric prism 70. Thereby, there is a degree of allowance in the heights of the light transmitting spaces, that is, the lengths of the first light transmitting spaces 71a and the second light transmitting spaces 71b in the direction along the z axis. Accordingly, portions that block entrance of measuring light beams having angular widths are further reduced, and the sensor chip C7 is favorable for use as a sensor chip in the case that the fan beam L' is employed as the measuring light beam.

Further, the sensor chip C7 of the fifth embodiment is provided with the second light transmitting surface 70d. Thereby, detection of the reflected light Lr' is facilitated. Accordingly, the sensor chip C7 of the fifth embodiment is a favorable sensor chip, particularly for use in SPR measurement.

Design Modifications to the Fifth Embodiment

In the sensor chip C7 having the first protective member and the second protective member, the protective members need not be of the same type, in a manner similar to the sensor chip C4 of the second embodiment.

Design Modifications to the First Through Fifth Embodiments

The sensor chips of the first through fifth embodiments have been described as being of configurations in which the detecting portions have metal films. However, the present invention is not limited to these configurations. That is, in the case that fluorometry is performed by evanescent excitation, the sensor chip can achieve the objective of the present invention even if it is not equipped with a detecting portion having a metal film. However, it is preferable for the detecting portion to have a metal film, because signal intensities can be amplified by an enhancing electric field formed due to surface plasmon.

Further, the protective members are not limited to those which are integrally formed with the dielectric prism or the lid member. That is, the protective member may be integrally formed with a third member that constitutes a sensor chip. Examples of such a third member include a member which is mounted on the lid member, and an intermediate member, which is mounted between the dielectric prism and the lid member.

Detecting Apparatus and Detecting Method

Figure 8:
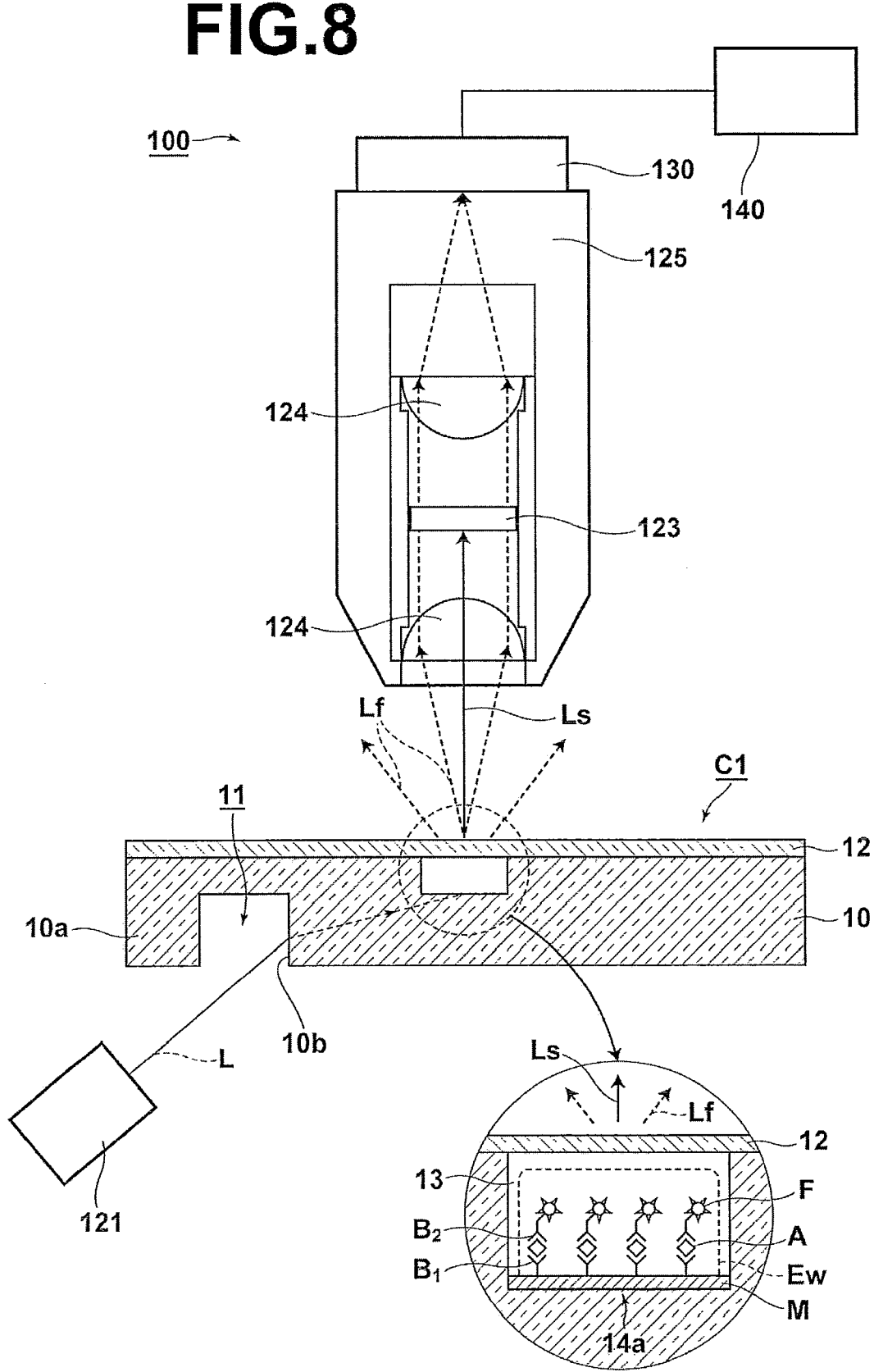
FIG. 8 is a diagram that illustrates the schematic structure of a fluorescence detecting apparatus that employs the sensor chip of the present invention.

FIG. 8 is a diagram that illustrates the schematic structure of a fluorescence detecting apparatus that employs the sensor chip C1 of the first embodiment. Note that the detecting apparatus that employ the sensor chip of the present invention is not limited to the fluorescence detecting apparatus illustrated in FIG. 8.

As illustrated in FIG. 8, the fluorescence detecting apparatus is equipped with: the total reflection illuminated sensor chip C1 of the first embodiment; a light source 121 that emits a measuring light beam L having a wavelength of 657 nm that excites fluorescent labels F; a photodetector 130 for detecting fluorescence Lf emitted by the fluorescent labels F which are supplied onto the sensor chip C1; two planoconvex lenses 124 which are arranged so as to guide the fluorescence Lf to the photodetector 130; an optical filter 123 provided between the two planoconvex lenses 124, for cutting off scattered light Ls of an electric field enhancing field Ew while transmitting the fluorescence Lf; and a data processing section 140 which is connected to the photodetector 130. Here, the light source 121 is provided beneath the sensor chip C1, such that the electric field enhancing field Ew is generated on the sensor chip C1. The fluorescent labels F are immobilized onto the metal film 14a via primary antibodies B1, antigens A and secondary antibodies B2. In addition, reference numeral 125 in FIG. 8 denotes an optical system holding portion, in which the two planoconvex lenses 124 and the optical filter 123 are contained, and to which the photodetector 130 is mounted.

The light source 121 is not particularly limited, and may be a laser light source. The type of light source to be employed as the light source 121 may be appropriately selected according to detection conditions. As described previously, the light source 121 is arranged such that the measuring light beam L output thereby enters the interface between the dielectric prism and the metal film of the sensor chip C1 at a resonance angle that causes total reflection at the interface, and such that surface plasmon resonance occurs at the metal film. Further, a light guiding member may be provided between the light source 121 and the sensor chip C1 as necessary. Note that it is preferable for the measuring light beam L to enter the interface in a P polarized state, such that surface plasmon can be induced.

The photodetector 130 is not limited, as long as it is capable of quantitatively detecting the fluorescence Lf emitted by the fluorescent labels F included in a sample S. The photodetector 130 may be selected appropriately according to detection conditions. Examples of photodetectors to be employed as the photodetector 130 include: CCD's, PD's (photodiodes); photomultipliers; and c-MOS's. In addition, the photodetector may be employed in combination with light dividing means, such as an optical filter or a spectroscope, according to detection conditions. Here, the optical filter 123 that cuts off the scattered light Ls and transmits the fluorescence Lf is provided between the two planoconvex lenses 124. Thereby, the fluorescence Lf can be efficiently detected while suppressing noise. That is, the fluorescence Lf can separated from the scattered light Ls and detected. Note that LAS-1000 manufactured by FUJIFILM Corporation is an example of an apparatus equipped with the optical system holding section 125, the two planoconvex lenses 124, the optical filter 123 and the photodetector 130, and can be favorably employed.

The data processing section 140 functions to process fluorescent signal data detected by the photodetector 130. A personal computer is an example of the data processing section 140. Note that the data processing section 140 is not limited to being a personal computer, and may be any electronic calculator or the like, as long as it serves the functions of the data processing section 140.

Hereinafter, a fluorescence detecting method of the present invention will be described for a case in which the fluorescence detecting apparatus described above is employed to detect antigens A from within a sample S that includes the antigens A.

A case will be considered in which antigens A are detected from within a sample S that includes the antigens A as a detection target substance.

The fluorescence detecting method employed here performs an assay by the sandwich method to be described later. The fluorescent labels F are immobilized onto the metal film 14a via the primary antibodies B1, the antigens A and the secondary antibodies B2. The measuring light beam L emitted by the light source 121 is caused to enter the interface between the dielectric prism and the metal film of the sensor chip C1 at a specific incident angle greater than or equal to a total reflection angle, to excite evanescent waves. The evanescent waves are caused to resonate with free electrons within the metal film 14a, to generate surface plasmon in the metal film 14a. The fluorescent labels F are excited by the enhancing electric field Ef formed due to the surface plasmon, to generate the fluorescence Lf. The fluorescence Lf is detected by the photodetector 130, and the fluorescent intensity is processed by the data processing section 140.

In the case described above, the presence of the fluorescent labels F is actually directly confirmed by the detection of fluorescence. However, it is considered that the fluorescent labels F would not be immobilized onto the metal film 14a unless the antigens A are present. Therefore, the presence of the antigens A, is indirectly confirmed by confirming the presence of the fluorescent labels F.

The primary antibodies B1 are not particularly limited, and may be appropriately selected according to detection conditions (particularly according to the targets of detection). For example, in the case that the antigens are CRP antigens (molecular weight: 110,000 Da), monoclonal antibodies (having different epitopes from the secondary antibodies B2 at least) that specifically bind with the antigens 2 may be employed as the primary antibodies B1. Known techniques may be employed to immobilize the primary antibodies B1 onto the metal film 14a.

The fluorescent labels F are not particularly limited, as long as they emit the fluorescence Lf of a predetermined wavelength when excited by the measuring light beam L. The fluorescent labels F may be selected appropriately according to measurement conditions (such as the detection target substance and the wavelength of the excitation light beam). In the case that the wavelength of the measuring light beam L is approximately 650 nm, Cy5 pigment (fluorescence: 680 nm, fluorescence quantum yield: 0.3) may be employed, for example.

The enhancing electric field Ew is an electric field which is formed by surface plasmon generated within the metal film 14a. The enhancing electric field Ew is amplified to a greater degree than evanescent waves which are generated at local regions on the metal film 14a. The enhancing electric field Ew amplifies signals, such as fluorescence emitted from the fluorescent labels. Surface plasmon is generated within the metal film 14a by evanescent waves and free electrons within the metal film 14a being caused to resonate.

The assay performed according to the sandwich method that immobilizes the fluorescent labels F onto the metal film 14a is performed by the following steps. The procedures by which an assay is performed according to the sandwich method to detect whether an antigen to be detected is included in blood (whole blood) will be described with reference to FIG. 9.

Figure 9:
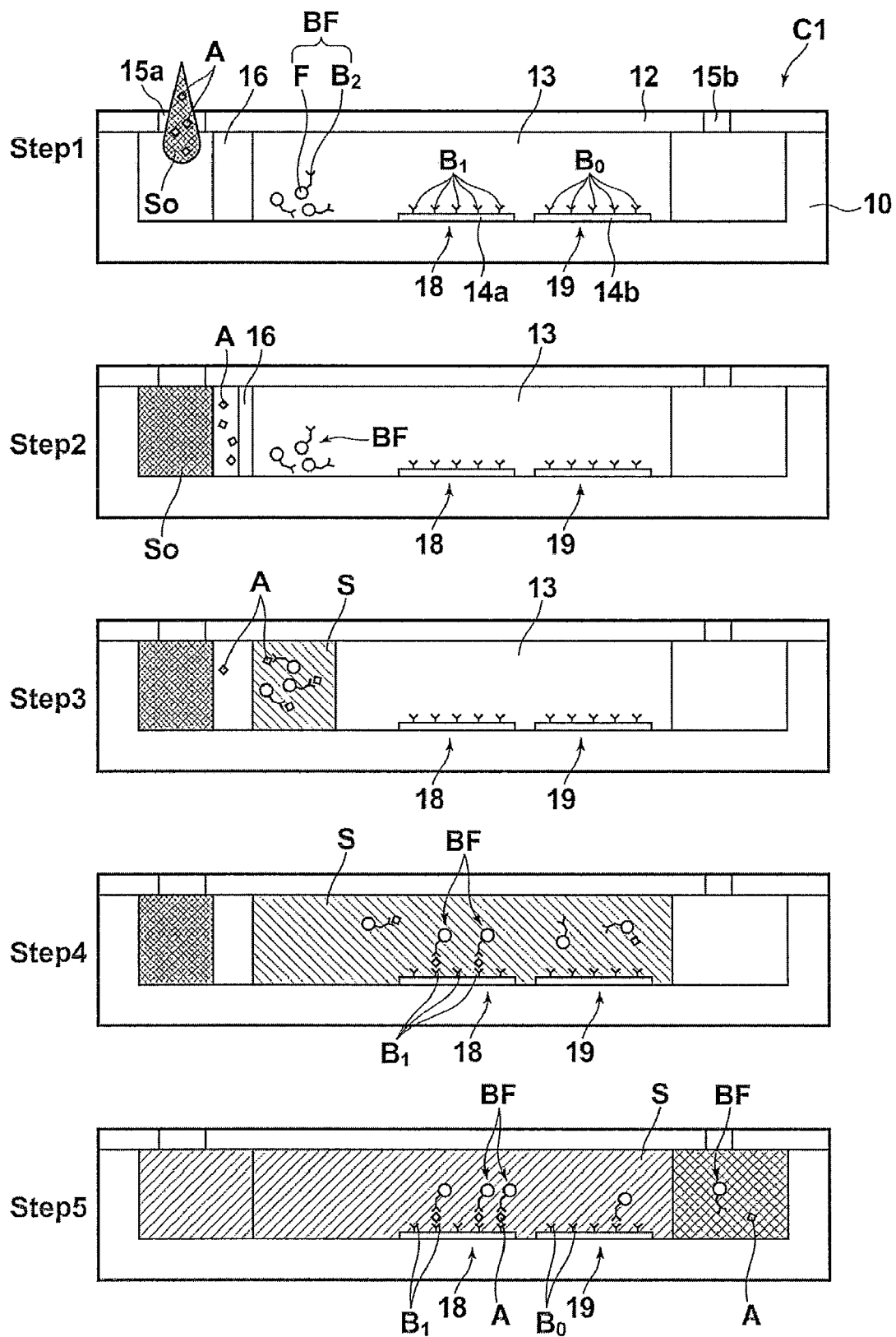
FIG. 9 is a collection of sectional views that illustrate the steps of an assay performed according to the sandwich method.

Step 1: The blood So (whole blood), which is the target of inspection, is injected through the injection opening 15a. Here, a case will be described in which the blood So includes the antigen A to be detected. In FIG. 9, the blood So is represented by the cross hatched regions.

Step 2: The blood So is filtered by a membrane filter 16, and large molecules, such as red blood cells and white blood cells, are separated as residue. Thereafter, plasma S (the blood from which blood cells have been filtered out by the membrane filter 16) leaks out into the flow channel 13 by capillary action. Alternatively, in order to expedite reactions and to shorten detection time, a pump may be connected to the air aperture 15b, and the plasma S may be caused to flow by suctioning and extruding operations of the pump. In FIG. 9, the plasma S is represented by the hatched regions.

Step 3: The plasma S that leaks into the flow channel 13 and labeling secondary antibodies BF, which have been provided upstream of the detecting portion within the flow channel in a dry state, are mixed, and the antigens A within the plasma S bind with the labeling secondary antibodies BF.

Step 4: The plasma S gradually flows along the flow channel 13 toward the air aperture 15b, and the antigens A which are bound to the labeling secondary antibodies BF bind with the primary antibodies B1 which are immobilized onto a measurement sensor portion 18, to form sandwich configurations, in which the antigens A are sandwiched between the primary antibodies B1 and the labeling secondary antibodies BF.

Step 5: A portion of the labeling secondary antibodies BF that did not bind with the antigens A bind with the primary antibodies B1 which are immobilized onto a reference detecting portion 19. Further, even in the case that the labeling secondary antibodies BF which did not bind with the antigens A or the primary antibodies B0 remain, the following plasma S functions as a cleansing agent that washes the labeling secondary antibodies BF, which are floating above the detecting portions, away.

In this manner, the blood So is injected through the injection opening 15a, and step 1 through step 5 are performed to cause the antigens to bind with the primary antibodies and the secondary antibodies. Thereafter, fluorescent signals are detected at the measurement detecting portion 18, to detect the presence and/or the concentration of the antigens at high sensitivity. Next, the sensor chip C1 is moved so as to enable fluorescent signal detection at the reference detecting portion 19, and fluorescent signals are detected at the reference detecting portion 19. The fluorescent signals obtained at the reference detecting portion 19, at which the primary antibodies B0 that bind with the labeling secondary antibodies BF are immobilized, are considered to be fluorescent signals that reflect reaction conditions such as the amount of the labeling secondary antibodies BF which has flowed through the flow channel 13 and the activity thereof. Therefore, if the fluorescent signals obtained at the reference detecting portion 19 are used as a reference to correct the fluorescent signals obtained at the measurement detecting portion 18, more accurate detection results can be obtained. In addition, a known amount of the labeling substance (fluorescent substance or fine metallic particles) may be immobilized onto the reference detecting portion 19 in advance, and the fluorescent signals obtained at the reference detecting portion 19 may be used as a reference to correct the fluorescent signals obtained at the measurement detecting portion.

The fluorescence detecting apparatus and the fluorescence detecting method described above employ the total reflection illuminated sensor chip of the present invention as the sensor chip. Accordingly, damage and contamination of the dielectric prism when the sensor chip is being handled during measurement can be prevented, and measurements can be performed at low cost.

(Design Modifications to the Detecting Apparatus and Detecting Method)

A detecting apparatus and a detecting method that perform fluorometry have been described above. The sensor chip of the present invention may also be applied to an SPR measuring apparatus, as illustrated in FIG. 10. In this case, it is preferable for a sensor chip having a second light transmitting surface and a second protective member, such as the sensor chips of the second and fifth embodiments, to be employed. FIG. 10 illustrates an example in which the sensor chip C4 of the second embodiment is employed. The SPR measuring apparatus 200 of FIG. 10 is equipped with: the sensor chip C4; a light source 221 for emitting a measuring light beam L of a wavelength that can induce surface plasmon at the metal film 44a such that conditions for total reflection are satisfied at the interface between the dielectric prism 40 and the metal film 44a (detecting portion); and a photodetector 222 which is provided to detect reflected light Lr. This SPR measuring apparatus 200 can be employed to perform SPR measurement. Details of the SPR measuring method are described in Japanese Patent No. 3562912 and U.S. Patent Application Publication No. 20060159591, for example.

As described above, damage and contamination of the second light transmitting surface can be prevented. Thereby, the reflected light Lr can be accurately detected, and SPR measurement having high quantitative properties can be performed without labels and in real time.

What is claimed is:

1. A total reflection illuminated sensor chip, which is employed in a detecting method for detecting a detection target substance comprising the steps of: supplying a sample that includes the detection target substance onto a detecting portion formed on a surface of a dielectric prism, irradiating a measuring light beam onto the interface between the dielectric prism and the detecting portion through a first light transmitting surface of the dielectric prism such that conditions for total reflection are satisfied at the interface, and utilizing evanescent waves which are generated at the detecting portion due to the irradiation of the measuring light beam to detect the detection target substance, the total reflection illuminated sensor chip comprising:
   the dielectric prism;
   the detecting portion formed on the surface of the dielectric prism; and
   a first protective member for protecting the first light transmitting surface;
   the first protective member being provided at a position which is a predetermined distance away from the first light transmitting surface so as to form a first light transmitting space, which is open at least toward the downward direction, between the first light transmitting surface and the first protective member; and
   the total reflection illuminated sensor chip being configured such that the interface can be irradiated by the measuring light beam that enters the first light transmitting space from below the first light transmitting space and passes through the first light transmitting surface.

2. A total reflection illuminated sensor chip as defined in claim 1, wherein:
   the first protective member is of a tapered shape that causes the first light transmitting space to become larger toward the downward direction.

3. A total reflection illuminated sensor chip as defined in claim 1, wherein:
   the first protective member is formed integrally with the dielectric prism.

4. A total reflection illuminated sensor chip as defined in claim 1, further comprising:
   a lid member which is mounted above the dielectric prism; and wherein:
   the first protective member is integrally formed with the lid member.

5. A total reflection illuminated sensor chip as defined in claim 1, further comprising:
   a second protective member, for protecting a second light transmitting surface of the dielectric prism, through which reflected light, which is the measuring light beam reflected at the interface, is output.

6. A total reflection illuminated sensor chip as defined in claim 5, wherein:

the second protective member is provided at a position which is a predetermined distance away from the second light transmitting surface so as to form a second light transmitting space, which is open at least toward the downward direction, between the second light transmitting surface and the second protective member; and the total reflection illuminated sensor chip is configured such that the reflected light that enters the second light transmitting space through the second light transmitting surface and passes beneath the second light transmitting space can be detected by a photodetector.

7. A total reflection illuminated sensor chip as defined in claim 5, wherein:

the second protective member is of a tapered shape that causes the second light transmitting space to become larger toward the downward direction.

8. A total reflection illuminated sensor chip as defined in claim 5, wherein:

the second protective member is formed integrally with the dielectric prism.

9. A total reflection illuminated sensor chip as defined in claim 5, further comprising:

a lid member which is mounted above the dielectric prism; and wherein:

the second protective member is integrally formed with the lid member.

10. A total reflection illuminated sensor chip as defined in claim 1, wherein:

a metal film is provided adjacent to the dielectric prism at the detecting portion; and the detecting method that the total reflection illuminated sensor chip is employed in utilizes an enhanced electric field caused by surface plasmon which is generated within the metal film due to the evanescent waves.

11. A total reflection illuminated sensor chip, which is employed in a detecting method for detecting a detection target substance comprising the steps of: supplying a sample that includes the detection target substance onto a detecting portion formed on a surface of a dielectric prism, irradiating a measuring light beam onto the interface between the dielectric prism and the detecting portion through a first light transmitting surface of the dielectric prism such that conditions for total reflection are satisfied at the interface, and utilizing evanescent waves which are generated at the detecting portion due to the irradiation of the measuring light beam to detect the detection target substance, the total reflection illuminated sensor chip comprising:

the dielectric prism;

the detecting portion formed on the surface of the dielectric prism; and a first protective member for protecting the first light transmitting surface;

the first protective member being provided so as to form a first light transmitting space having the shape of a cutout which is open at least toward the downward and forward directions and which communicates with the first light transmitting surface in the rearward direction; and the total reflection illuminated sensor chip being configured such that the interface can be irradiated by the measuring light beam that passes through the first light transmitting space and the first light transmitting surface.

12. A total reflection illuminated sensor chip as defined in claim 11, wherein:

the first protective member is formed integrally with the dielectric prism.

13. A total reflection illuminated sensor chip as defined in claim 11, further comprising:

a lid member which is mounted above the dielectric prism; and wherein:

the first protective member is integrally formed with the lid member.

14. A total reflection illuminated sensor chip as defined in claim 11, further comprising:

a second protective member, for protecting a second light transmitting surface of the dielectric prism, through which reflected light, which is the measuring light beam reflected at the interface, is output.

15. A total reflection illuminated sensor chip as defined in claim 14, wherein:

the second protective member is provided so as to form a second light transmitting space having the shape of a cutout which is open at least toward the downward and forward directions and which communicates with the second light transmitting surface in the rearward direction; and the total reflection illuminated sensor chip is configured such that the reflected light that passes through the second light transmitting surface and the second light transmitting space can be detected by a photodetector.

16. A total reflection illuminated sensor chip as defined in claim 14, wherein:

the second protective member is formed integrally with the dielectric prism.

17. A total reflection illuminated sensor chip as defined in claim 14, further comprising:

a lid member which is mounted above the dielectric prism; and wherein:

the second protective member is integrally formed with the lid member.

18. A total reflection illuminated sensor chip as defined in claim 11, wherein:

a metal film is provided adjacent to the dielectric prism at the detecting portion; and the detecting method that the total reflection illuminated sensor chip is employed in utilizes an enhanced electric field caused by surface plasmon which is generated within the metal film due to the evanescent waves.

* * * * *